United States Patent [19]

Protiva et al.

[11] 4,238,611
[45] Dec. 9, 1980

[54] POLYSUBSTITUTED DERIVATIVES OF 10-PIPERAZINODIBENZO (B,F) THIEPINE

[75] Inventors: Miroslav Protiva; Karel Sindelar; Irena Cervena; Jirina Metysova, all of Prague, Czechoslovakia

[73] Assignee: SPOFA, United Pharmaceutical Works, Prague, Czechoslovakia

[21] Appl. No.: 646,755

[22] Filed: Jan. 6, 1976

[30] Foreign Application Priority Data

Jan. 6, 1975 [CS] Czechoslovakia .................. 95/75

[51] Int. Cl.³ ........................................ C07D 409/04
[52] U.S. Cl. .................................. 544/375; 424/250
[58] Field of Search ................ 260/268 TR; 544/375

[56] References Cited

U.S. PATENT DOCUMENTS

| | | | |
|---|---|---|---|
| B 539,374 | 3/1976 | Gerecke et al. | 260/268 TR |
| 3,928,383 | 12/1975 | Kaplan et al. | 260/268 TR |
| 3,954,769 | 5/1976 | Gerecke et al. | 260/268 TR |
| 3,966,737 | 6/1976 | Gerecke et al. | 260/268 TR |
| 4,011,222 | 3/1977 | Gerecke et al. | 260/268 TR |

FOREIGN PATENT DOCUMENTS 1093910  12/1967  United Kingdom .

*Primary Examiner*—Jose Tovar

[57] ABSTRACT

Polysubstituted derivatives of 10-piperazinodibenzo (b,f) thiepine and processes for the preparation thereof are described. The compositions evidence psychotropic and antimicrobial characteristics and are of low toxicity. The described compounds are of the general formula

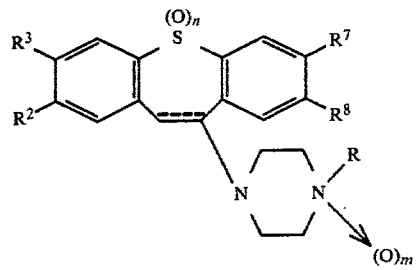

wherein $R^2$, $R^3$, $R^7$ and $R^8$ are selected from among hydrogen, fluorine and chlorine atoms, a fluoromethyl group, a methoxy group and a hydroxyl group, at least three of $R^2$, $R^3$, $R^7$ and $R^8$ being other than hydrogen, R being selected from among hydrogen, alkyl or alkylhydroxy groups having from 1–3 carbon atoms, an acyloxyalkyl group having from 8–10 carbon atoms in the acyl moiety and from 2–3 carbon atoms in the alkyl moiety and an ethoxycarbonyl group, m and n representing integers from 0–1 and the bond between the 10 and 11 carbon atoms being either a single or double bond.

12 Claims, No Drawings

POLYSUBSTITUTED DERIVATIVES OF 10-PIPERAZINODIBENZO (b,f) THIEPINE

This invention relates to therapeutically useful derivatives of dibenzo (b,f) thiepine and to a process for the preparation thereof. More particularly, the present invention relates to polysubstituted derivatives of 10-piperazinodibenzo (b,f) thiepine and to a process for preparing same, such compositions evidencing psychotropic and antimicrobial characteristics.

In accordance with the present invention, the polysubstituted derivatives of 10-piperazinodibenzo (b,f) thiepine are of the general formula

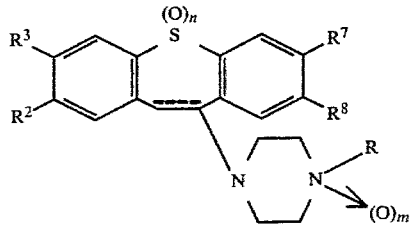
(1)

wherein $R^2$, $R^3$, $R^7$ and $R^8$ are selected from the group consisting of hydrogen, fluorine and chlorine atoms, a fluoromethyl group, a methoxy group and a hydroxyl group, at least three of said $R^2$, $R^3$, $R^7$ and $R^8$ substituents are other than hydrogen, R being selected from the group consisting of hydrogen, an alkyl group having from 1-3 carbon atoms, an alkylhydroxy group having from 1-3 carbon atoms, an acyloxyalkyl group having from 8-10 carbon atoms in the acyl moiety and from 2-3 carbon atoms in the alkyl moiety, and an ethoxycarbonyl group, m and n representing integers from 0-1 and the bond between the number 10 and 11 carbon atoms being single or double. The invention also is directed to salts of the foregoing compositions.

As indicated above, studies of the described compounds have revealed their psychotropic activity, and in light of their limited toxicity, application in the psychiatric and neurological fields is indicated.

The subject compositions are most conveniently prepared in diverse procedures dependent upon the values of n and m, the nature of the bond between the number 10 and 11 carbon atoms and the nature of the substituents in the $R^2$, $R^3$, $R^7$, $R^8$ and R positions. Thus, the following generic reactions may be employed to this end:

(a) Compounds of the general formula (1) wherein the 10-11 carbon bond is a double bond, n and m are zero and $R^2$, $R^3$, $R^7$, $R^8$ and R are as designated above and may be prepared by reaction of a ketone of the general formula

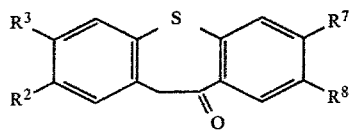
(2)

wherein $R^2$, $R^3$, $R^7$ and $R^8$ are as designated above with a piperazine derivative of the general formula

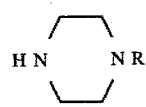
(3)

wherein R is as designated above, water produced during the course of the reaction being continuously removed by azeotropic distillation of the reaction mixture with toluene or xylene in the presence of an acidic catalyst, such as p-toluenesulfonic acid and the like.

The described compound may also be prepared by a modified enamine synthesis wherein compound (2) and compound (3) are heated in boiling benzene in the presence of an equivalent amount of titanium tetrachloride, or by heating mixtures of compound (2) with mono-salts of compound (3) in vacuum at a temperature ranging from 190°-200° C. The latter reaction is of particular interest because of its rapidity, completion being attained after several hours.

(b) Compounds of the general formula (1) wherein the 10-11 carbon bond is a single bond and n and m are zero are prepared by a substitution reaction wherein chlorides of the general formula

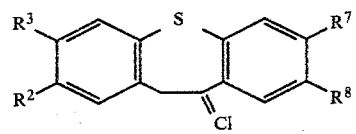
(4)

wherein $R^2$, $R^3$, $R^7$ and $R^8$ are as designated in formula (1) with piperazine derivatives of formula (3). One procedure for effecting this reaction involves reacting the chlorides of formula (4) with at least a 100 percent excess of piperazine (3) in boiling chloroform, the piperazine serving as a condensation agent. The reaction may also be conducted in the absence of a solvent by heating chloride (4) with 100% excess of piperazine (3) to a temperature ranging from 80°-100° C.

Under certain circumstances, namely, when using highly reactive chlorides (4), ($R^7$=OCH$_3$), are employed, reaction may be effected at room temperature. The substitution reaction may also occur using equimolar amounts of chlorides (4) and piperazine (3) by employing a condensation agent in benzene, dimethylformamide and the like. Suitable condensation agents for this purpose are triethylamine, pyridine, alkali metal carbonates and the like.

(c) Compounds of the general formula (1) wherein the 10-11 carbon bond is a single bond and n and m are zero may also be prepared by reduction of analogous compounds containing a 10-11 double bond. This end may be attained by the use of reducing agents such as zinc in acetic acid, diborane generated in situ by reaction of sodium borohydride with acetic acid in tetrahydrofuran, and the like.

(d) Compounds of the general formula (1) wherein the 10-11 carbon bond is a single bond, n and m are zero and at least one of the $R^2$, $R^3$, $R^7$ and $R^8$ radicals is a free hydroxyl group may be prepared by demethylation of analogous methoxy derivatives, typically by reaction with boron tribromide in chloroform at room temperature.

(e) Compounds of the general formula (1) wherein n and m equal zero and R is an acyloxyalkyl group may be prepared from analogous compounds wherein R is a hydroxyalkyl group by esterification with saturated free fatty acids containing a straight chain of from 8–10 carbon atoms or with reactive derivatives thereof. When using free acids, the esterification is effected by means of an azeotropic distillation with benzene, toluene or xylene in the presence of an acid catalyst such as p-toluenesulfonic acid and the like, water produced during the reaction being continuously removed.

Reactive derivatives of fatty acids include the chlorides which react either in the presence of condensation agents such as pyridine or in their absence in the presence of a solvent such as benzene. The use of fatty acid esters as the acylating derivatives necessitates transesterification, volatile lower alcohols produced in the base catalyzed reaction being removed from the reaction mixture.

(f) Compounds of the general formula (1) wherein n and m equal zero and R is hydrogen may be prepared by hydrolysis of the corresponding compounds wherein R is an ethoxycarbonyl group, alkaline hydrolysis being preferred.

(g) Compounds of the general formula (1) wherein m is 1 may be prepared from the corresponding amines (m=0) by oxidation of alcoholic solutions of the bases with hydrogen peroxide.

(h) Compounds of the general formula (1) wherein n is 1 and m is zero may be prepared from the corresponding sulfides (n=0) by oxidation of aqueous solutions of their soluble salts, such as the methanesulfonates, with hydrogen peroxide at room temperature.

The compositions of interest, that is, the 10-piperazinodibenzo (b,f) thiepines, are basic in nature and may readily be neutralized with organic or inorganic acids to yield corresponding salts which are also novel. These salts crystallize readily and are soluble in water, so suggesting their use in pharmacological testing and in the formulation of diverse medicaments. As such, the salts are considered superior to the bases for this purpose.

Several examples of the invention are set forth below. It will be appreciated by those skilled in the art that the examplary embodiments are for purposes of exposition only and are not to be construed as limiting.

EXAMPLE 1

2,3-Dimethoxy-10-(4-methylpiperazino)dibenzo (b,f) thiepine

A solution of titanium tetrachloride (1.5 g) in benzene (10 ml) was added dropwise during 10 minutes to a stirred solution of 2,3-dimethoxydibenzo(b,f)thiepine-10(11H)-one (2.85 g) and 1-methylpiperazine (7.5 g) in benzene (20 ml) and the resulting mixture stirred for 50 hours at room temperature. The mixture was then decomposed with water, the separated solid filtered by suction, the benzene layer in the filtrate separated, washed with water, dried and taken down. Next, the oily non-homogeneous residue was dissolved in a small amount of boiling methanol. The desired product (0.92 g) crystallized on standing and was purified by crystallization from a benzene-light petroleum mixture, m.p. 211°–211.5° C.

The starting 2,3-dimethoxydibenzo(b,f)thiepine-10(11H)-one is a new compound which can be prepared, e.g., from the known 2-iodo-4,5-dimethoxyphenylacetic acid (R.I.T. Cromartie et al: J. Chem. Soc. 1958, 1982) by the following procedure:

Thiophenol (16 g) is dissolved while stirring in a warm solution of potassium hydroxide (26 g) in water (260 ml). 2-Iodo-4,5-dimethoxyphenylacetic acid (42.5 g) and freshly reduced copper (2 g) are added to this solution and the mixture refluxed for 7 hours while stirring. The warm reaction mixture is filtered with charcoal and the cooled filtrate acidified with hydrochloric acid. Next day, the separated crude 2-(phenylthio)-4,5-dimethoxyphenylacetic acid is filtered with suction, washed with water, dried and crystallized from benzene, affording 35.8 g of the pure product, m.p. 143°–145° C.

Ethanol (40 ml) is added dropwise to a stirred suspension of phosphorus pentoxide (80 g) in benzene (600 ml) and the mixture was stirred for 1 hour. The acid from the above preparation (36 g) was added to the thus-prepared phosphate and the mixture refluxed for 7 hours. Next day, the benzene layer is decanted from the cold mixture, the residue washed with benzene, the benzene solutions combined, washed with 5% sodium hydroxide solution and water, and dried. The solvent was distilled off and the oily residue was dissolved in a mixture of benzene-light petroleum (30 ml). On standing, the desired 2,3-dimethoxydibenzo(b,f)thiepine-10(11H)-one (20.3 g) crystallizes in the higher-melting modification, m.p. 127°–129° C. Crystallization from cyclohexane affords the lower-melting form, m.p. 116°–118° C.

EXAMPLE 2

2,3-Dimethoxy-10-(4-methylpiperazino)-10,11-dihydrodibenzo(b,f)thiepine

A mixture of 10-chloro-2,3-dimethoxy-10,11-dihydrodibenzo(b,f)thiepine (8.4 g), chloroform (30 ml) and 1-methylpiperazine (30 ml) was warmed until a homogeneous solution forms. Then, it was allowed to stand for 4 weeks. The reaction mixture was next diluted with benzene and thoroughly washed with water. The organic layer was shaken with an excess of 5% hydrochloric acid, the acid aqueous layer separated, made alkaline by addition of ammonium hydroxide and the required base isolated by extraction with benzene. The work-up of the extract yielded 10.5 g of the crystalline solvate of the base, containing a half molecule of crystal benzene, m.p. 64°–69° C. (benzene-light petroleum). Neutralization of this base with maleic acid in ethanol yields crystalline dimaleate hemihydrate, m.p. 121°–122° C. (ethanol).

The required starting 10-chloro-2,3-dimethoxy-10,11-dihydrodibenzo(b,f)thiepine has not been described as yet in the literature. It can be prepared, e.g., from 2,3-dimethoxydibenzo(b,f)thiepine-10(11H)-one, the preparation of which is described in Example 1, by the following procedure:

A solution of sodium borohydride (2.27 g) in water (5 ml), to which 1 drop of 20% sodium hydroxide solution was added, was added dropwise at 25° C. to a solution of the ketone (11.4 g) in dioxane (150 ml). The mixture was stirred for 4 hours at room temperature, set aside overnight, then diluted with water, acidified with hydrochloric acid (7 ml), allowed to stand in a refrigerator for 2 hours and the separated solid filtered. The product was essentially pure 10-hydroxy-2,3-dimethoxy-10,11-dihydrodibenzo(b,f)thiepine (10.7 g; 93%) which was crystallized from a chloroform-benzene mixture, m.p. 161.5°–162° C.

A solution of the alcohol from the preceding experiment (9.0 g) in dichloromethane (100 ml) was cooled to 0° C., powdered anhydrous calcium chloride (6 g) added and anhydrous hydrogen chloride introduced under cooling into the resultant suspension for 2.5 hours. The mixture was then stirred at 0° C. for 3 hours, filtered and the filtrate taken down in vacuo. Crystallization of the residue from benzene and work-up of the mother liquors yielded 8.45 g (88%) of the required 10-chloro-2,3-dimethoxy-10,11-dihydrodibenzo(b,f)-thiepine, m.p. 155°–160° C.

EXAMPLE 3

2,3-Dihydroxy-10-(4-methylpiperazino)-10,11-dihydrodibenzo(b,f)thiepine

A solution of boron tribromide (19.6 g) in chloroform (15 ml) was added dropwise under nitrogen during 15 minutes at 20° C. to a solution of 2,3-dimethoxy-10-(4-methylpiperazino)-10,11-dihydrodibenzo(b,f)thiepine (solvate of the base with a half molecule of crystal benzene; see the preceding Example) (10.5 g) in chloroform (40 ml). The mixture was stirred at room temperature for 5 hours. Then, ethanol (50 ml) was added dropwise under cooling and stirring continued for another 8 hours. Next day, the mixture was diluted with ether (90 ml) and the precipitated crude dihydrobromide of the product (11.5 g) filtered. Crystallization from a mixture of 95% ethanol and ether yields its dihydrate, m.p. 160°–161° C. (decomposition). On standing in dilute aqueous solution, this salt undergoes partial hydrolysis, so resulting in a partially soluble monohydrobromide which separates from solution. This salt crystallizes from a mixture of 95% ethanol and ether and melts at 228°–230° C. (decomposition).

EXAMPLE 4

8-Chloro-2,3-dimethoxy-10-(4-methylpiperazino)-10,11-dihydrodibenzo(b,f)thiepine A mixture of 8,10-dichloro-2,3-dimethoxy-10,11-dihydrodibenzo(b,f)thiepine(15.6 g), chloroform (30 ml) and 1-methylpiperazine (30 ml) was warmed until a homogeneous solution was formed. The solution was allowed to stand for 48 hours, refluxed for 8 hours, cooled, diluted with benzene and thoroughly washed with water. The benzene solution was next shaken with an excess of 5% hydrochloric acid, the separated solid hydrochloride filtered and combined with the aqueous phase of the filtrate. Addition of ammonium hydroxide liberated the base which was extracted with benzene. The benzene extract was dried over anhydrous potassium carbonate and taken down, leaving 15.0 g of the desired crude base which was purified by crystallization from benzene-light petroleum, m.p. 169°–172° C. Neutralization of the base with methanesulfonic acid in a mixture of ethanol and ether yielded crystalline dimethanesulfonate which in the pure state melts at 188.5°–189.5° C. (ethanol-ether).

The required starting 8,10-dichloro-2,3-dimethoxy-10,11-dihydrodibenzo(b,f)thiepine is a new compound which can be prepared, e.g., from the known 2-iodo-4,5-dimethoxyphenylacetic acid (see Example 1) by the following procedure:

4-Chlorothiophenol (25.0 g) is dissolved under stirring in a solution of potassium hydroxide (30.7 g) in water (300 ml). 2-Iodo-4,5-dimethoxyphenylacetic acid (50.0 g) and copper (3.1 g) were added and the stirred mixture refluxed for 6 hours. It is filtered when hot, the filtrate cooled and acidified by addition of hydrochloric acid. The precipitated crude 2-(4-chlorophenylthio)-4,5-dimethoxyphenylacetic acid was filtered, washed with water, dried and crystallized from benzene, affording 47.1 g of the pure compound, m.p.131°–133° C.

Anhydrous ethanol (50 ml) was added dropwise under stirring to a mixture of phosphorus pentoxide (100 g) and benzene (800 ml) and the resulting mixture was refluxed for 45 minutes. The acid from the preceding experiment (46 g) was added to the thus-prepared phosphate ester and the mixture refluxed for 6 hours. After standing overnight, the benzene layer was decanted and the residue extracted with boiling benzene (300 ml, boiling for 2 hours). The benzene solutions were combined, washed with 5% sodium hydroxide solution and with water, dried over magnesium sulfate and taken down, leaving 39 g of an oily neutral product which was dissolved in hot benzene. On addition of light petroleum, the solution deposits crystals of 8-chloro-2,3-dimethoxydibenzo(b,f)thiepine-10(11H)-one (23.0 g). A sample of this compound was purified by crystallization from a benzene-ethanol mixture; m.p. 178°–179° C.

A solution of sodium borohydride (3.2 g) in water (7 ml), to which 3 drops of 20% sodium hydroxide solution were added, is added dropwise to a solution of the ketone from the preceding preparation (20.7 g) in dioxane (220 ml) and the mixture is stirred for 6 hours at room temperature. Next day, the mixture is diluted with large amounts of water, acidified with hydrochloric acid (9 ml) and the separated crude 8-chloro-10-hydroxy-2,3-dimethoxy-10,11-dihydrodibenzo(b,f)thiepine filtered and purified by crystallization from benzene-light petroleum; m.p. 125°–127° C., yield 19.0 g.

Calcium chloride (4.0 g) is added to a solution of the above alcohol (7.62 g) in dichloromethane (100 ml) and anhydrous hydrogen chloride is introduced into this mixture at 0° C. for 3 hours. Then the mixture is stirred for 3 hours at room temperature, filtered and the filtrate taken down under diminished pressure, yielding the desired 8,10-dichloro-2,3-dimethoxy-10,11-dihydrodibenzo(b,f)thiepine in quantitative yield (7.95 g). This product is crystallized from benzene-light petroleum and melts at 139°–141° C.

EXAMPLE 5

8-Chloro-2,3-dihydroxy-10-(4-methylpiperazino)-10,11-dihydrodibenzo(b,f)thiepine A solution of boron tribromide (7.9 g) in chloroform (5 ml) was added dropwise at 20° C. during 15 minutes to a solution of 8-chloro-2,3-dimethoxy-10-(4-methylpiperazino)-10,11-dihydrodibenzo(b,f)thiepine (4.26 g) (see Example 4) in chloroform (15 ml) and the mixture stirred for 6 hours at room temperature. Next day, the mixture was decomposed under external cooling, by addition of ethanol (20 ml), stirred for 8 hours and set aside overnight. Upon dilution with ether (40 ml), the separated crude dihydrobromide of the product was filtered with suction and crystallized from aqueous ethanol, yielding 2.63 g of the pure dihydrobromide dihydrate, m.p. 173°–175° C. (decomposition).

EXAMPLE 6

8-Chloro-2,3-dimethoxy-10-(4-methylpiperazino)-10,11-dihydrodibenzo(b,f)thiepine-5-oxide A solution of 8-chloro-2,3-dimethoxy-10-(4-methylpiperazino)-10,11-dihydrodibenzo(b,f)thiepine dimethanesulfonate (8.5 g) (see Example 4) in water (50 ml) was treated with 30% hydrogen peroxide (16 ml) and the mixture allowed to stand for 20 hours at room temperature. Addition of ammonium hydroxide liberated the base which was extracted with benzene. The extract affords an oily residue which crystallized from a mixture of benzene-light petroleum, m.p. 178°–179° C., yield 3.70 g of the desired base.

EXAMPLE 7

8-Chloro-2,3-dimethoxy-10-(4-methylpiperazino)-10,11-dihydrodibenzo(b,f)thiepine-N-oxide A solution of the base of 8-chloro-2,3-dimethoxy-10-(4-methylpiperazino)-10,11-dihydrodibenzo(b,f)thiepine (see Example 4) (5.0 g) in ethanol (25 ml) and dioxane (10 ml) was treated with 30% hydrogen peroxide (2.5 ml). The mixture was set aside overnight and then refluxed for 3 hours. The excess hydrogen peroxide destroyed by heating with platinum foil and the solution taken down in vacuo. The residue was diluted with water, acidified with hydrochloric acid, filtered and the filtrate again taken down. Crystallization of the residue from a mixture of 95% ethanol and ether yields 5.4 g of the dihydrochloride dihydrate of the desired base, m.p. 177°–179° C.

EXAMPLE 8

7,8-Dichloro-10-(4-methylpiperazino)-10,11-dihydrodibenzo(b,f)thiepine

A mixture of 7,8,10-trichloro-10,11-dihydrodibenzo(b,f)thiepine (6.31 g) and 1-methylpiperazine (6.0 g) was heated to 110°–120° C. for 4.5 hours. The reaction mixture was then cooled and shaken with benzene and water, the benzene layer separated and shaken with an excess of 5% hydrochloric acid. The formed solid hydrochloride was filtered, combined with the acid aqueous layer of the filtrate and the resultant suspension made basic with ammonium hydroxide. The liberated base was isolated by extraction with benzene. The benzene extract yielded 3.2 g (42%) of the crystalline base, melting at 130°–132° C. (ethanol). Neutralization of this base with maleic acid in ethanol yields the crystalline maleate, m.p. 163°–166° C. (ethanol).

The required starting 7,8,10-trichloro-10,11-dihydrodibenzo(b,f)thiepine has not hitherto been described in the literature. It can be prepared, e.g., from the known 3,4-dichlorothiophenol (see L. Almasi et al: Acad. Rep. Populare Romine, Filiala Cluj, Studii Cercetari Chim. 12, No. 1, 165, 1961; Chem. Abstr. 58, 4456 e, 1963) by the following reaction sequence:

3,4-Dichlorothiophenol (38 g) is dissolved in a solution of potassium hydroxide (41 g) in water (430 ml). Then o-iodo-benzoic acid (52.3 g) and copper (1.5 g) are added and this mixture is refluxed under stirring for 7 hours. The mixture is filtered while hot, the filtrate acidified with hydrochloric acid and allowed to stand overnight. The resulting 2-(3,4-dichlorophenylthio)benzoic acid (37.9 g; 61%) is then filtered, m.p. 240°–240.5° C. (ethanol).

A 70% benzene solution (240 g) of sodium bis(2-methoxyethoxy)aluminum hydride is added dropwise during one hour to a stirred suspension of the above acid (125 g) in benzene (800 ml) and the reaction mixture is stirred for 2 hours at room temperature. Next day, it is decomposed by a slow addition of an excess of 10% sodium hydroxide solution. The usual work-up of the benzene layer affords 94 g of 2-(3,4-dichlorophenylthio)benzyl alcohol as an oily liquid, boiling at 188°–191° C./0.4 Torr.

Thionyl chloride (50 g) is added dropwise during one hour at 10°–20° C. to a stirred mixture of the above alcohol (93.8 g) and pyridine (33.2 g). The mixture is stirred for 4 hours at room temperature and 2 hours at 40°–50° C. Next day, it is decomposed with water and the product is taken up in benzene. The usual work-up of the extract affords 102 g (theoretical amount) of the crude oily 2-(3,4-dichlorophenylthio)benzyl chloride. For characterization, a sample of the product is distilled, b.p. 176° C./0.9 Torr. The crude residue is used in the further work.

A solution of sodium cyanide (26.2 g) in water (40 ml) was added to a solution of the crude chloride from the preceding experiment (108.5 g) in ethanol (110 ml), the mixture refluxed for 8 hours and allowed to stand overnight. The ethanol was distilled off in vacuo, the residue diluted with water and the product taken up in benzene. The benzene extract yields 90 g of crude 2-(3,4-dichlorophenylthio)phenylacetonitrile, which is distilled at 192°–196° C./0.4 Torr. The distillate sets to crystals on standing, m.p. 48°–49° C. (ethanol).

The nitrile from the preceding experiment (70.9 g) is added to a solution of potassium hydroxide (60 g) in ethanol (220 ml) and water (130 ml) and the mixture refluxed for 8 hours. Ethanol is evaporated in vacuo, the residue diluted with water, the hot solution filtered with charcoal and the filtrate made acidic with hydrochloric acid. After standing overnight, the separated 2-(3,4-dichlorophenylthio)-phenylacetic acid (60.7 g; 80%) is filtered, m.p. 105°–107° C. (benzene-light petroleum).

The acid from the preceding experiment (68 g) is added to polyphosphoric acid, prepared from phosphorus pentoxide (160 g) and 77% phosphoric acid (170 g), and the mixture is heated to 115°–120° C. for 4 hours under stirring. The reaction mixture is cooled, decomposed with an excess of ice and water and the product isolated by extraction with benzene. The extract is washed with 5% sodium hydroxide solution and water, dried and taken down, leaving 41.4 g (65%) of 6,7-dichlorodibenzo(b,f)thiepine-10(11H)-one, m.p. 133°–135° C. (benzene-ethanol).

A solution of the ketone from the preceding experiment (14.8 g) in a mixture of benzene (50 ml) and ethanol (150 ml) is reduced by adding dropwise a solution of sodium borohydride (0.88 g) in water (10 ml) to which 0.1 ml of 15% sodium hydroxide solution has been added. The mixture is refluxed for 4.5 hours, the solvents are evaporated under diminished pressure, the residue diluted with water and the product isolated by extraction with benzene. The benzene extract yields 12.7 g (85%) of 7,8-dichloro-10-hydroxy-10,11-dihydrodibenzo(b,f)thiepine, m.p. 124°–126° C. (ethanol).

Powdered anhydrous calcium chloride (15 g) is added to a solution of the alcohol from the preceding experiment (17.9 g) in benzene (150 ml) and anhydrous hydrogen chloride is passed into this suspension for 4 hours under stirring. After standing overnight, the mixture is filtered, the filtrate is taken down under diminished pressure and the residue is crystallized from benzene (20 ml), yielding 17.4 g (92%) of 7,8,10-trichloro-10,11-dihydrodibenzo(b,f)thiepine, m.p. 130°–131° C.

EXAMPLE 9

7,8-Dichloro-10-[4-(3-hydroxypropyl)-piperazino]10,11-dihydrodibenzo(b,f)thiepine A mixture of 7,8,10-trichloro-10,11dihydrodibenzo(b,f)thiepine (the preparation of which is described in the preceding Example) (16.2 g) and 1-(3-hydroxypropyl)piperazine (21.6 g) were heated to 110°–120° C. for 4.5 hours. The procedure is analogous to that described for preparation of the final base in the preceding Example and yields 12.3 g (57%) of the crystalline base, m.p. 126°–128° C. (ethanol). Neutralization with methanesulfonic acid in ethanol yields crystalline monohydrate of dimethanesulfonate, $C_{23}H_{34}Cl_2N_2O_8S_3$ which is crystallized from ethanol and melts at 198°–200° C.

EXAMPLE 10

7,8-Dichloro-10-(4-ethoxycarbonylpiperazino)-10,11-dihydrodibenzo(b,f)thiepine

A mixture of 7,8,10-trichloro-10,11-dihydrodibenzo(b,f)thiepine (the preparation of which is described in Example 8) (9.5 g) and 1-ethoxycarbonylpiperazine (11.9 g) was heated to 110°–120° C. for 4 hours. The preparation of the reaction mixture is analogous to that used in the preparation of the final base in Example 8 and yields 10.8 g (82%) of an oily base which was dissolved in ethanol and neutralized with maleic acid. Addition of either precipitates the maleate, $C_{25}H_{26}Cl_2N_2O_6S$ which is crystallized from a ten-fold amount of ethanol and melts at 184°–186° C.

EXAMPLE 11

7,8-Dichloro-10-piperazino-10,11-dihydrodibenzo(b,f)thiepine

A mixture of 7,8,10-trichloro-10,11-dihydrodibenzo(b,f)thiepine (see Example 8) (6.3 g) and anhydrous piperazine (20 g) was heated to 110°–120° C. for 5 hours. The reaction mixture was shaken with water and benzene and the benzene layer worked up as described in Example 8 for the preparation of the final base, yielding 3.0 g of the crystalline base $C_{18}H_{18}Cl_2N_2S$, m.p. 131°–133° C. (after crystallization from acetone).

The same product was prepared by the following procedure: A mixture of crude 7,8-dichloro-10-(4-ethoxycarbonylpiperazino)-10,11-dihydrodibenzo(b,f)thiepine (3.5 g) (prepared according to the preceding Example), potassium hydroxide (1.75 g) and ethanol (3.5 ml) was refluxed for 3 hours in a bath heated to 120°–125° C. The reaction mixture was cooled and shaken with benzene and water. The isolation procedure is the same as described in the preceding Examples, yielding the crude base in an almost theoretical yield. On crystallization from acetone it melts at 131°–133° C.

EXAMPLE 12

7,8-Dichloro-10-(4-methylpiperazino)dibenzo(b,f)thiepine

1-Methylpiperazine (15.0 g), followed by titanium tetrachloride (3.1 g) in benzene (45 ml), was added to a warm solution of 7,8-dichlorodibenzo(b,f)thiepine-10(11H)-one (8.85 g) (its preparation is described in Example 8) in benzene (75 ml). The mixture was refluxed while stirring for 28 hours, cooled and decomposed with water (100 ml). The resultant precipitate was filtered and washed with benzene and water. The benzene layer in the filtrate was separated, washed with water, dried over magnesium sulfate and taken down. The enamine base, obtained in nearly quantitative yield, was purified by crystallization from ethanol, m.p. 157°–159° C. Neutralization with maleic acid in ethanol yields the maleate, $C_{23}H_{22}Cl_2N_2O_4S$, which is crystallized from ethanol; m.p. 229°–232° C.

EXAMPLE 13

7,8-Dichloro-10-(4-methylpiperazino)-10,11-dihydrodibenzo(b,f)thiepine

Sodium borohydride (1.4 g) was added to a solution of 7,8-dichloro-10-(4-methylpiperazino)dibenzo(b,f)thiepine (5.3 g) (the preparation of which is described in the preceding Example) in tetrahydrofuran (25 ml). Then, acetic acid (10 ml) was added dropwise and the mixture refluxed for 3 hours, cooled, diluted with chloroform, washed with 2 N-NaOH (15 ml) and with water. The organic layer yields the crude crystalline residue, consisting of the desired base (m.p. 131°–132° C.) (identical with the product described in Example 8). Its neutralization with maleic acid in ethanol yielded the maleate, m.p. 163°–166° C. (ethanol), which is also identical with the corresponding product described in Example 8.

EXAMPLE 14

7,8-Dichloro-10-[4-(3-capryloyloxypropyl)piperazino]-10,11-dihydrodibenzo(b,f)thiepine Capryloly chloride (10.6 g) was added to a warm solution of 7,8-dichloro-10-[4-(3-hydroxypropyl)piperazino]-10,11-dihydrodibenzo(b,f)thiepine (the product of the reaction described in Example 9) (12.7 g) in benzene (40 ml). The mixture was allowed to stand for 48 hours at room temperature and then heated to 60° C. for 1 hour. The mixture was cooled, diluted with benzene (250 ml), the solution washed rapidly with ice-cold 5% sodium hydroxide solution (150 ml) and with water, dried over sodium sulfate and taken down. The oily residue, which represents the crude base of the ester, was dissolved in acetone (35 ml) and the solution neutralized by addition of a solution of maleic acid (8.5 g) in acetone (40 ml). The mixture yielded 19.2 g of the dihydrogen maleate, $C_{37}H_{46}Cl_2N_2O_{10}S$, which is crystallized from acetone; m.p. 144°–147° C.

EXAMPLE 15

7,8-Difluoro-10-(4-methylpiperazino)-10,11-dihydrodibenzo(b,f)thiepine

A mixture of 7,8-difluoro-10-chloro-10,11-dihydrodibenzo(b,f)thiepine (5.08 g), 1-methylpiperazine (4 ml) and chloroform (5 ml) was refluxed for 7 hours. Chloroform was evaporated and the residue shaken with water and benzene. The organic layer was washed with water and shaken with dilute (1:2) hydrochlorid acid (50 ml). The formed suspension was filtered and the thus-obtained solid hydrochloride added to the aqueous layer of the filtrate. Addition of 15% sodium hydroxide solution liberated the desired base which was extracted with benzene, m.p. 106°–108° C. (acetone). Neutralization of this base with methanesulfonic or maleic acid in ethanol, followed by the addition of ether, yields the corresponding salts, i.e., the methanesulfonate (m.p. 244°–247° C.) or maleate (hemihydrate, m.p. 161°–163° C.), which were purified by crystallization from a mixture of ethanol and ether.

The starting 7,8-difluoro-10-chloro-10,11-dihydrodibenzo(b,f)thiepine has not been described as yet in the literature. It can be prepared from the known 3,4-difluorobromobenzene (see A. Roe et al: J. Org. Chem. 21, 28, 1956) by the following synthesis:

A solution of Grignard reagent is prepared from 3,4-difluorobromobenzene (23.0 g) and magnesium (3.18 g) in ether (65 ml). After cooling to 20° C., flowers of sulphur (3.0 g) are added to the Grignard reagent, the mixture stirred for 1 hour at room temperature and, after standing overnight, it is slowly decomposed by addition of dilute (1:1) hydrochloric acid (100 ml) and extracted with benzene. The product is taken from the benzene solution into an excess of 10% sodium hydroxide solution from which it is again liberated by addition of dilute hydrochloric acid, and finally is taken up in benzene. The benzene solution is dried over sodium sulfate, taken down and the residue distilled, yielding the desired 3,4-difluorothiophenol, b.p. 70° C./13 Torr. Oxidation of the higher-boiling fractions affords a small amount of bis(3,4-difluorophenyl)disulfide as a yellow liquid, b.p. 135°–140° C./18 Torr.

The above diol (13.2 g), followed by o-iodophenylacetic acid (23.7 g) and "molecular" copper (0.7 g), is added to a solution of potassium hydroxide (17.2 g) in water (180 ml). The resulting mixture is refluxed for 7 hours, filtered while hot and the filtrate cooled and acidified with dilute hydrochloric acid. Upon standing overnight at room temperature, the product which originally separated as an oil sets to crystals. It is filtered, washed with water and air-dried, yielding 22.8 g (90%) of 2-(3,4-difluorophenylthio)phenylacetic acid which is crystallized from hexane; m.p. 54°–57° C.

A mixture of the acid from the preceding preparation (3.44 g) and polyphosphoric acid (25.1 g) is heated for 6 hours, the temperature of the bath being 115°–125° C. Then the mixture is decomposed by pouring into ice and water (100 g) and the product is taken up in benzene. The benzene extract is washed with 5% sodium hydroxide solution and dried over sodium sulfate. Evaporation of the solvent yields 2.81 g (87%) of the crude 7,8-difluorodibenzo(b,f)thiepine-10(11H)-one which crystallizes from ethanol and in analytically pure state melts at 110°–112° C.

A solution of sodium borohydride (0.42 g) in water (4 ml), containing 0.1 ml of 15% sodium hydroxide solution, is slowly added dropwise to a solution of the ketone from the preceding preparation (6.56 g) in benzene (50 ml) and ethanol (60 ml) and the mixture is refluxed for 3 hours. The solvent is distilled off under reduced pressure, the residue is shaken with benzene and water and the benzene layer separated, washed with 5% hydrochloric acid, 3% sodium hydroxide and water, dried over sodium sulfate and taken down, leaving crude 7,8-difluoro-10-hydroxy-10,11-dihydrodibenzo(b,f)thiepine in practically theoretical yield (6.68 g). The product is purified by crystallization from cyclohexane; m.p. 98°–100° C.

A stream of anhydrous hydrogen chloride is passed at room temperature for 1.5 hours into a solution of the alcohol prepared in the preceding experiment (5.32 g) in benzene (50 ml) to which anhydrous calcium chloride (3.5 g) has been added. After standing for 24 hours, the benzene is evaporated under diminished pressure and the crystalline residue is purified by crystallization from ethanol, yielding 4.88 g (86%) of 7,8-difluoro-10-chloro-10,11-dihydrodibenzo(b,f)thiepine, m.p. 68°–71° C.

EXAMPLE 16

7,8-Difluoro-10-(4-methylpiperazino(dibenzo(b,f)thiepine

1-Methylpiperazine (16 g), followed by titanium tetrachloride (3.1 g) in benzene (25 ml) was added to a warm solution of 7,8-difluorodibenzo(b,f)thiepine-10(11H)-one (the preparation of which is described in Example 15) (7.87 g) in benzene (75 ml). The mixture was stirred and refluxed for 25 hours, cooled and decomposed with water (100 ml). The precipitated solid was filtered and washed with benzene and water. The benzene layer of the filtrate was separated, washed with water, dried over sodium sulfate and taken down, leaving the crystalline enamine base in an almost theoretical yield (10.2 g). The product was purified by crystallization from ethanol, m.p. 118°–120° C. Neutralization with methanesulfonic acid yielded the crystalline methanesulfonate, m.p. 297°–300° C. (aqueous ethanol).

EXAMPLE 17

7,8-Difluoro-10-[4-(2-hydroxyethyl)piperazino]-10,11-dihydrodibenzo(b,f)thiepine A mixture of 7,8-difluoro-10-chloro-10,11-dihydrodibenzo(b,f)thiepine (see Example 15) (6.35 g), 1-(2-hydroxyethyl)-piperazine (6.1 g) and chloroform (10 ml) was refluxed for 7.5 hours under stirring. The chloroform was evaporated under diminished pressure, the residue dissolved in benzene (200 ml) and the solution thoroughly washed with water and shaken with 3 N-HCl (150 ml). The precipitated hydrochloride was filtered, added to the aqueous layer of the filtrate and the resultant suspension made alkaline by addition of ammonium hydroxide. The liberated base was taken up in benzene and the extract yielded 7.1 g (84%) of the desired oily base. This was crystallized from aqueous acetone in the form of the hemihydrate, which in the pure state melts at 101°–102° C.

EXAMPLE 18

7,8-Difluoro-10-[4-(2-hydroxyethyl)piperazino]-10,11-dihydrodibenzo(b,f)thiepine-$N^4$-oxide A solution of the hemihydrate of 7,8-difluoro-10-[4-(2-hydroxyethyl)piperazino]-10,11-dihydrodibenzo(b,f)thiepine (see the preceding Example) (5.22 g) in ethanol (30 ml) was treated with 27% hydrogen peroxide (3.7 ml) and the mixture refluxed for 3 hours. Then, a small piece of platinum foil was added and the mixture refluxed for one hour to destroy the excess hydrogen peroxide. The solution was taken down under diminished pressure, benzene added to the residue and the evaporation repeated in order to remove the water. The residue (5.4 g; 100%) represents the amorphous N-oxide base which was neutralized with hydrogen chloride in a mixture of ethanol and ether, yielding the crystalline dihydrochloride, m.p. 156°–157° C. (aqueous ethanol). The presence of the N-oxide group was proved polarographically.

EXAMPLE 19

7-Fluoro-8-chloro-10-(4-methylpiperazino)-10,11-dihydrodibenzo(b,f)thiepine

A mixture of 7-fluoro-8,10-dichloro-10,11-dihydrodibenzo(b,f)thiepine (7.48 g), 1-methylpiperazine (5.2 ml) and chloroform (7 ml) was refluxed for 7 hours. The chloroform was evaporated and the residue taken up in water (20 ml) and benzene (80 ml). The benzene solution was washed with water and shaken with 3 N-HCl (100 ml). The separated hydrochloride was filtered and added to the aqueous layer of the filtrate. The resulting suspension was made alkaline with ammonium hydroxide and the liberated base taken up in benzene. The desired product, m.p. 105°–107° C. (acetone), was obtained in 74% yield (6.66 g). Its neutralization with maleic acid in ethanol, followed by addition of ether, yielded the crystalline maleate, m.p. 168°–169° C. (ethanol).

The required starting 7-fluoro-8,10-dichloro-10,11-dihydrodibenzo(b,f)thiepine was not described as yet in the literature. It can be prepared, e.g., from the known 2-chloro-5-bromoaniline (see B. R. Suthers et al: J. Org. Chem. 27, 447, 1962) by the following procedure:

2-Chloro-5-bromoaniline (258 g) is added to concentrated hydrochloric acid (750 ml) and the mixture is stirred at 80°–90° C. until formation of a homogeneous suspension. Then, it is cooled and diazotized at 0°–5° C. by dropwise addition of sodium nitrite (95.1 g) in water (330 ml) during 1 hour. The mixture is stirred for an additional 20 minutes and then a solution of fluoroboric acid (700 ml) (prepared by dissolving 264 g of boric acid in 744 ml of 40% hydrofluoric acid) is added. After 30 minutes of stirring, the separated fluoroborate was filtered, washed successively with a small amount of a fluoroboric acid solution, ethanol and ether, and dried thoroughly in air and in vacuo. The thermal decomposition of the fluoroborate is carried out in two portions. Each portion is heated in a flask with a direct flame, the internal temperature during the decomposition being 130°–170° C. The distillates are combined and shaken with water (250 ml) and ether (250 ml). The ethereal layer is washed with 10% sodium hydroxide solution, 3 N-HCl and water and dried over sodium sulfate. The ether is evaporated and the residue is distilled, yielding 184.2 g (70%) of 2-chloro-5-bromofluorobenzene, b.p. 130°–142° C./20 Torr.

Reaction of 2-chloro-5-bromofluorobenzene (84.6 g) with magnesium (10.7 g) in ether (200 ml) yields a solution of Grignard reagent. This is cooled to 20°–25° C. and powdered sulfur (10 g) is added portionwise during 80 minutes while stirring. The mixture is diluted with ether (100 ml), stirred for one hour at room temperature and then set aside overnight. Next day, the mixture is decomposed by dropwise addition of dilute (1:1) hydrochloric acid (200 ml) while stirring. On addition of ether, the ethereal layer is separated and the product is taken up in an excess of 10% sodium hydroxide solution. The aqueous layer, containing the sodium salt of the product, is separated, acidified by addition of hydrochloric acid and the liberated 3-fluoro-4-chlorothiophenol is taken up in benzene, b.p. 97°–98° C./Torr, yield 35.7 g (54%).

The thiol from the preceding experiment (72.3 g), followed by o-iodobenzoic acid (98 g) and molecular copper (2.7 g), is added to a solution of potassium hydroxide (75 g) in water (800 ml). The mixture is stirred and refluxed for 7 hours, filtered while warm and the filtrate acidified by addition of concentrated hydrochloric acid (80 ml). After standing overnight, the product is filtered, washed with water, boiled with ethanol (800 ml), cooled, again filtered and dried, yielding 106 g (85%) of 2-(3-fluoro-4-chlorophenylthio)benzoic acid. A sample of the product is crystallized from a large volume of ethanol; m.p. 231°–232° C.

Sodium borohydrate (4.2 g) is slowly added under external cooling to a suspension of the thoroughly dried acid from the preceding experiment (28.3 g) in tetrahydrofuran (50 ml) and then boron trifluoride etherate (12.5 ml) is added dropwise to this mixture at 20°–30° C. during 20 minutes. The whole preparation is carried out under nitrogen. The mixture is stirred for 3 hours at room temperature, and after standing overnight, it is decomposed by addition of an excess of hydrochloric acid. Water (50 ml) and benzene (50 ml) are added and the mixture is filtered. The organic layer of the filtrate is separated, washed with 5% sodium hydroxide solution and with water, dried and taken down. Distillation of the residue yields 20.1 g (75%) of 2-(3-fluoro-4-chlorophenylthio)benzyl alcohol, b.p. 182°–186° C./0.9 Torr.

Thionyl chloride (25.4 g) is added dropwise at 10°–20° C. in the course of 30 minutes to a mixture of the alcohol from the preceding preparation (41.6 g) and pyridine (16 g). The mixture is stirred for 2 hours at room temperature, then for 1 hour at 30°–40° C., cooled and cautiously decomposed by dropwise addition of water (75 ml). The mixture is extracted with benzene, the extract is washed with dilute hydrochloric acid and water, dried over calcium chloride and taken down, yielding 40.2 g (90%) of the crude 2-(3-fluoro-4-chlorophenylthio)benzyl chloride. For analysis, a small sample is distilled, b.p. 159°–160° C./1 Torr.

A solution of sodium cyanide (12.6 g) in water (20 ml) is added to a solution of the crude chloride, from the preceding experiment, (49.1 g) in ethanol (50 ml) and the mixture is refluxed for 13 hours. The ethanol is evaporated, the residue is shaken with water (100 ml) and benzene (250 ml), and the benzene layer is washed with water, dried and taken down. The crystalline residue is mixed with ethanol and filtered, yielding 38.2 g (81%) of crude 2-(3-fluoro-4-chlorophenylthio)-phenylacetonitrile which, upon crystallization from ethanol melts at 80°–81° C.

A solution of the nitrile from the preceding experiment (44.5 g) in ethanol (150 ml) is mixed with a solution of potassium hydroxide (40 g) in water (90 ml) and this mixture is refluxed for 4 hours. The ethanol is evaporated and the residue is diluted with water (500 ml), the solution then being washed with benzene and filtered with charcoal. The filtrate is acidified with an excess of hydrochloric acid, and, after standing overnight, the separated 2-(3-fluoro-4-chlorophenylthio)-phenylacetic acid is filtered, washed with water and air-dried; yield—45.4 g (95%). Crystallization from benzene yields the product melting at 118°–119° C.

A mixture of polyphosphoric acid (155 g) and the acid from the preceding preparation (28.8 g) was heated to 115°–125° C. for 4 hours while stirring. The reaction mixture was cooled, decomposed with ice and water (500 ml) and the separated product extracted with warm benzene. The extract was washed with 5% sodium hydroxide solution and water, dried and taken down. The resultant crude 7-fluoro-8-chlorodibenzo(b,f)thiepine-10(11H)-one is crystallized from ethanol (500 ml), yielding 22.5 g (83%) of the product, m.p. 126°–128° C.

The ketone from the preceding preparation (13.9 g) was dissolved in warm ethanol (200 ml), the solution cooled and treated with a solution of sodium borohydride (0.9 g) in water (7 ml) to which 20% sodium hydroxide (0.1 ml) has been added. The mixture was refluxed for 3.5 hours while stirring, the ethanol evaporated under diminished pressure and the residue shaken with water (150 ml) and benzene (150 ml). The benzene layer was washed with 3% sodium hydroxide solution and water, dried and taken down, leaving 12.5 g (89%) of crude 7-fluoro-8-chloro-10-hydroxy-10,11-dihydrodibenzo(b,f)thiepine, which was crystallized from hexane; m.p. 69°–71° C.

Anhydrous calcium chloride (5.0 g) was added to a solution of the alcohol from the preceding preparation (5.62 g) in benzene (70 ml). Anhydrous hydrogen chloride was passed into this suspension for 2 hours. After standing overnight, the mixture is filtered and the filtrate taken down in vacuo, yielding crystalline 7-fluoro-8,10-dichloro-10,11-dihydrodibenzo(b,f)thiepine in an almost theoretical yield (5.8 g). Crystallization from acetone affords the analytically pure product, m.p. 94°–96° C.

EXAMPLE 20

7-Fluoro-8-chloro-10-(4-methylpiperazino)dibenzo(b,f)thiepine

1-Methylpiperazine (20 g), followed by a solution of titanium tetrachloride (4.2 g) in benzene (30 ml) was added to a solution of 7-fluoro-8-chlorodibenzo(b,f)thiepine-10(11H)-one (the preparation of which is described in the preceding Example) (11.2 g) in benzene (100 ml). The mixture was refluxed for 25 hours under stirring, cooled and decomposed by dropwise addition of water (150 ml). The precipitated solid was removed by filtration and washed with benzene. The benzene layer of the filtrate was separated, washed with water, filtered with charcoal, dried and taken down. The residue represents an almost theoretical amount (14.0 g) of 7-fluoro-8-chloro-10-(4-methylpiperazino)dibenzo(b,f)thiepine. A sample was purified by crystallization from ethanol; m.p. 107°–108° C. Neutralization with maleic acid in ethanol yielded the maleate which, on crystallization from aqueous ethanol, melts at 215°–219° C.

EXAMPLE 21

7-Fluoro-8-chloro-10-[4-(2-hydroxyethyl)piperazino]-10,11-dihydrodibenzo(b,f)thiepine A mixture of 7-fluoro-8,10-dichloro-10,11-dihydrodibenzo(b,f)thiepine (the preparation of which is described in Example 19) (4.5 g), 1-(2-hydroxyethyl)piperazine (4.1 g) and chloroform (5 ml) was refluxed for 7.5 hours. The reaction mixture was then diluted with chloroform (50 ml) and the solution washed with water. The chloroform was evaporated the residue dissolved in benzene (200 ml) and the solution shaken with 3 N-HCl (60 ml). The separated hydrochloride was filtered, suspended in the aqueous layer of the filtrate and the suspension made basic with ammonium hydroxide. The liberated base was taken up in chloroform and isolated as usual; m.p. 150°–152° C. (acetone), yield 4.8 g (81%).

EXAMPLE 22

7-Fluoro-8-chloro-10-[4-(2-caprinoyloxyethyl)-piperazino]-10,11-dihydrodibenzo(b,f)thiepine Caprinoyl chloride (4.6 g) was added to a solution of 7-fluoro-8-chloro-10-[4-(2-hydroxyethyl)piperazino]-10,11-dihydrodibenzo(b,f)thiepine (the preparation of which is described in the preceding example) (3.93 g) in chloroform (30 ml). The mixture was allowed to stand for 24 hours at room temperature, then decomposed with water (30 ml) and diluted with chloroform. The organic layer was washed with an ice-cold dilute sodium hydroxide solution and water, dried over potassium carbonate and taken down. The residue (7.2 g) was chromatographed on an alumina column (150 g), the desired ester(4.67 g) being eluted with benzene. Neutralization with maleic acid in acetone yielded di(hydrogen maleate) which is crystallized from acetone and melts at 125°–127° C.

EXAMPLE 23

7-Fluoro-8-chloro-10-[4-(2-hydroxyethyl)piperazino]-10,11-dihydrodibenzo(b,f)thiepine-$N^4$-oxide To a solution of 7-fluoro-8-chloro-10-[4-(2-hydroxyethyl)piperazino]-10,11-dihydrodibenzo(b,f)thiepine (the preparation of which is described in Example 21) (8.6 g of the free base) in ethanol (40 ml) 25% hydrogen peroxide (4.0 ml) was added and the mixture refluxed for 3 hours. The excess of hydrogen peroxide was removed by heating with platinum foil and the mixture taken down in vacuo. The residue was dissolved in ethanol, the solution filtered and the filtrate again taken down under diminished pressure, yielding the crystalline crude N-oxide (8.8 g, about 100%). This is crystallized from aqueous acetone and forms a monohydrate which melts in the pure state at 186°–189° C. Neutralization with hydrogen chloride in a mixture of ethanol and ether affords the dihydrochloride which crystallizes from aqueous ethanol as a hemihydrate, m.p. 167°–170° C.

EXAMPLE 24

7-Chloro-8-fluoro-10-(4-methylpiperazino)-10,11-dihydrodibenzo(b,f)thiepine

A mixture of 7,10-dichloro-8-fluoro-10,11-dihydrodibenzo(b,f)thiepine (5.19 g), 1-methylpiperazine (4.0 ml) and chloroform (10 ml) was refluxed for 8 hours. The chloroform was evaporated under diminished pressure, the residue mixed with benzene (100 ml) and the solution washed thoroughly with water. The washed benzene solution was then shaken with an excess of 2 N-HCl, the separated hydrochloride filtered, added to the aqueous layer of the filtrate and this suspension made alkaline with ammonium hydroxide. The liberated base is taken up in benzene. The benzene extract yielded 4.52 g (71%) of an oily base which slowly crystallizes from cyclohexane or ethanol and which in the pure state melts at 137°–139° C. Neutralization of this base with maleic acid in ethanol, followed by addition of ether to the obtained solution, yielded the crystalline maleate which, on crystallization from a small volume of ethanol, melts at 171°–173° C.

The required starting 7,10-dichloro-8-fluoro-10,11-dihydrodibenzo(b,f)thiepine has not been described as yet in the literature. It can be prepared, e.g., from the known 2-chloro-4-bromoaniline (Chattaway and Orton, J. Chem. Soc. 79, 466, 1901; Ber. 33, 2398, 1900) by the following procedure:

Hydrochloric acid (110 ml) is added to a solution of 2-chloro-4-bromoaniline (35.3 g) in ethanol (30 ml), the resultant solution of the hydrochloride cooled in a freezing mixture to 0° C. and a solution of sodium nitrite (13.2 g) in water (45 ml) added dropwise at 0°–7° C. during 1.5 hours while stirring. The resultant solution of the diazonium salt is stirred for 15 minutes and then a solution of fluoroboric acid (prepared by dissolution of 44.6 g of boric acid in 127 ml of 40% hydrofluoric acid) (95 ml) is added. After 30 minutes of stirring at room temperature, the separated fluoroborate is filtered, washed with a small amount of fluoroboric acid solution and with ether, and air-dried. Thus, 36.3 g of 2-chloro-4-fluorobenzenediazonium fluoroborate, m.p. 160°–162° C., is obtained which decomposes at 185° C. The decomposition is carried out in a flask, equipped with an efficient downward condenser, the flask being heated with a direct flame. When the decomposition is complete, the whole apparatus is washed with ether, the ether washings are combined with the distillate, the ethereal solution washed with 20% sodium hydroxide solution and water, dried over sodium sulfate, taken down and the resulting 3-chloro-4-fluorobromobenzene (15.0 g) distilled, b.p. 93°–95° C./30 Torr.

Magnesium (22.1 g) under absolute ether (170 ml) is activated by addition of an iodine crystal and a solution of the chlorofluorobromobenzene from the preceding experiment (173 g) in ether (330 ml) is added dropwise during 1 hour while stirring. The preparation of the Grignard reagent is completed by boiling the mixture for 75 minutes. Powdered sulfur (20.6 g) is then added in small portions to the stirred mixture at 20°–25°C. during 2 hours. The mixture is allowed to stand for 48 hours and then decomposed while stirring by dropwise addition of dilute (1:1) hydrochloric acid (450 ml). The separated aqueous layer is extracted with benzene, the extract combined with the ethereal layer, shaken with an excess of 10% sodium hydroxide solution, into which the acidic product goes over. The organic layer is removed, the alkaline solution again acidified with hydrochloric acid and the liberated product extracted with benzene. The benzene extract yields 69.7 g (52%) of 3-chloro-4-fluorothiophenol, b.p. 100°–102° C./22 Torr.

The thiophenol from the preceding experiment (34.5 g) is added at 50° C. to a solution of potassium hydroxide (40 g) in water (425 ml) and this mixture is stirred until it becomes homogeneous. Then, o-iodophenylacetic acid (55.0 g) and copper powder (2.0 g) are added and the mixture refluxed for 24 hours. While still warm, the solution is filtered with charcoal, the filtrate diluted with water and acidified with hydrochloric acid. The separated crude oily acid is extracted with benzene, the solvent evaporated and the residue crystallized from aqueous ethanol, yielding 45.2 g (72%) of 2-(3-chloro-4-fluorophenylthio)phenylacetic acid which in the pure state melts at 85°–87° C. (cyclohexane-hexane).

A mixture of polyphosphoric acid (230 g) and the acid from the proceding preparation (22.6 g) was heated to 130°–140° C. for 4 hours under stirring. After cooling, it was decomposed with ice-cold water (750 ml) and extracted with benzene. The extract was washed with 5% sodium hydroxide solution and water, dried and taken down. The solid residue was crystallized from ethanol (600 ml), yielding 19.0 g (90%) of 7-chloro-8-fluorodibenzo(b,f)thiepine-10(11H)-one, m.p. 125°–126° C.

A solution of sodium borohydride (0.42 g) in water (4 ml), containing 15% sodium hydroxide solution (0.1 ml), was added dropwise to a solution of the ketone from the preceding experiment (7.0 g) in a mixture of ethanol (70 ml) and benzene (25 ml). The mixture was refluxed for 3 hours, diluted with water and extracted with benzene. The extract was washed with 5% sodium hydroxide solution and water, dried over sodium sulphate and taken down. The solid residue was crystallized from hexane (30 ml), yielding 6.60 g (94%) of 7-chloro-8-fluoro-10-hydroxy-10,11-dihydrodibenzo(b,f)thiepine, m.p. 86°–87° C.

Powdered anhydrous calcium chloride (8 g) was added to a solution of the product of the preceding preparation (7.9 g) in benzene (80 ml), and anhydrous hydrogen chloride introduced for 2 hours into this suspension while stirring. After standing overnight, the mixture was filtered and the filtrate taken down under diminished pressure, yielding 8.22 g (97%) of crude crystalline 7,10-dichloro-8-fluoro-10,11-dihydrodibenzo(b,f)thiepine. After one crystallization from cyclohexane, this product is obtained in the pure state; m.p. 108°–110° C.

EXAMPLE 25

7-Chloro-8-fluoro-10-[4-(2-hydroxyethyl)-piperazine]10,11-dihydrodibenzo(b,f)thiepine A mixture of 7,10-dichloro-8-fluoro-10,11-dihydrodibenzo(b,f)thiepine (see Example 24) (4.42 g), 1-(2-hydroxyethyl)piperazine (4.1 g) and chloroform (5 ml) was refluxed for 7.5 hours. The chloroform was evaporated, the residue dissolved in benzene (100 ml), washed thoroughly with water and shaken with an excess of 3 N-HCl. The separated solid hydrochloride was filtered, decomposed by addition of ammonium hydroxide, and the liberated base extracted with benzene. The benzene extract yielded 5.28 g (91%) of the crude oily base which was crystallized from cyclohexane as a solvate with a half cyclohexane molecule, m.p. 87°–91° C. Neutralization of this base with maleic acid in ethanol followed by addition of ether yielded the crystalline maleate, m.p. 167°–170° C.

EXAMPLE 26

7-Chloro-8-fluoro-10-(4-methylpiperazino)dibenzo(b,f)-thiepine

1-Methylpiperazine (18.2 ml) was added to a solution of 7-chloro-8-fluorodibenzo(b,f)thiepine-10(11H)-one (see Example 24) (10.16 g) in benzene (90 ml). To this mixture a solution of titanium tetrachloride (3.7 g) in benzene (30 ml) was added dropwise during 5 minutes. The mixture was refluxed for 24 hours, cooled and decomposed by addition of ice-cold water (150 ml). After 30 minutes' standing, the precipitated solid was filtered and washed with benzene. The aqueous layer of the filtrate was extracted with the same solvent, the benzene layers combined, washed with water, dried and taken down, leaving 12.1 g (91%) of the oily base which slowly crystallizes from ethanol. When pure, it melts at 158°–160° C. Neutralization with maleic acid in ethanol yielded the crystalline maleate, m.p. 228°–230° C. (aqueous ethanol).

EXAMPLE 27

7-Chloro-8-fluoro-10-[4-(2-hydroxyethyl)piperazino]-dibenzo(b,f)thiepine

A mixture of 7-chloro-8-fluorodibenzo(b,f)thiepine-10(11H)-one (see Example 24) (8.36 g), 1-(2-hydroxyethyl)piperazine (11.7 g) and p-toluenesulfonic acid (15.5 g) was heated in vacuo first for 1 hour to 180°–190° C. and then for 3 hours at 195° C. The mixture was cooled, made basic with ammonium hydroxide (50 ml) and extracted with benzene. The extract was washed with water, dried, taken down and the oily residue dissolved in boiling ethanol (40 ml). After cooling, the solution yielded a small amount of the starting ketone which was filtered off. The filtrate was taken down, leaving 10.9 g of the desired base which was transformed by neutralization with maleic acid in ethanol into its crystalline maleate, solvated with a half molecule of ethanol, m.p. 183°–185° C. The base, liberated from the maleate, was crystalline and melted at 144°–147° C. (acetone).

EXAMPLE 28

7-Trifluoromethyl-8-chloro-10-(4-methylpiperazino)-10,11-dihydrodibenzo(b,f)thiepine A mixture of 7-trifluoromethyl-8,10-dichloro-10,11-dihydrodibenzo(b,f)thiepine (2.89 g), 1-methylpiperazine (1.8 ml) and chloroform (2.5 ml) was refluxed for 7 hours. The chloroform was evaporated under diminished pressure, the residue dissolved in benzene (30 ml), washed with water, and the benzene layer separated and shaken with an excess of 3 N-HCl. The precipitated hydrochloride was filtered, added to the aqueous layer of the filtrate and the base liberated by addition of ammonium hydroxide. It was extracted with benzene and the conventional work-up procedure yielded 1.93 g (56%) of the crude 7-trifluoromethyl-8-chloro-10-(4-methylpiperazino)-10,11-dihydrodibenzo(b,f)thiepine. Neutralization with maleic acid in ethanol followed by addition of ether yielded the crystalline maleate which was crystallized from ethanol; m.p. 197°–200° C.

The required starting 7-trifluoromethyl-8,10-dichloro-10,11-dihydrodibenzo(b,f)thiepine has not been as yet described in the literature. It can be prepared, e.g., from the ketone 3-trifluoromethyl-4-chlorothiophenol (see French Pat. No. 1,481,052; Chem. Abstr. 69, 18 84Oh) by the following procedure:

3-Trifluoromethyl-4-chlorothiophenol (130 g) and o-iodobenzoic acid (152 g) are successively dissolved at 50° C. in a solution of potassium hydroxide (117 g) in water (1220 ml). Then molecular" copper (4.1 g) is added and the mixture refluxed for 7.5 hours under stirring. It is filtered while hot, the filtrate acidified with dilute hydrochloric acid and set aside overnight. The separated 2-(3-trifluoromethyl-4-chlorophenylthio)benzoic acid is filtered, washed with water and purified by crystallization from ethanol; m.p. 187°–189° C., yield 149 g (73%).

Sodium borohydride (10.3 g) is slowly added under nitrogen to a suspension of the acid from the preceding experiment (81 g) in tetrahydrofuran (125 ml), and then boron trifluoride etherate (32 ml) in tetrahydrofuran (20 ml) is added dropwise at 20° C. during 0.5 hour. The mixture is stirred for 3 hours at 20°–25° C. and allowed to stand at room temperature overnight. It is then decomposed by dropwise addition of an excess of dilute hydrochloric acid, washed with benzene (100 ml) and the mixture filtered. The benzene layer of the filtrate is separated, washed with 10% sodium hydroxide solution and water, dried over sodium sulfate and taken down. The residue is distilled, affording 66.1 g (85%) of 2-(3-trifluoromethyl-4-chlorophenylthio)benzyl alcohol, b.p. 160°–163° C./0.2 Torr.

The alcohol from the preceding preparation (86.5 g) is mixed with pyridine (27 g) and thionyl chloride (44.5 g) is added dropwise in the course of 1 hour, the temperature being maintained below 25° C. by external cooling. The mixture is stirred for 2 hours at room temperature and then for one hour at 30°–40° C., after cooling decomposed by addition of water (100 ml) and extracted with benzene. The extract is washed with dilute hydrochloric acid and water, dried over calcium chloride and evaporated. The residue (82 g; 90%) represents crude 2-(3-trifluoromethyl-4-chlorophenylthio)benzyl chloride; which distills without decomposition at 165°–167° C./0.8 Torr.

A solution of sodium cyanide (18.0 g) in water (30 ml) is added to a solution of the chloride from the preceding experiment (82.5 g) in ethanol (90 ml) and the mixture is refluxed for 15 hours. The ethanol is evaporated, the residue is diluted with water and the product is extracted with benzene. The benzene extract affords 44.8 g (56%) of 2-(3-trifluoromethyl-4-chlorophenylthio)-phenylacetonitrile, m.p. 69°–70° C. (ethanol).

A solution of the nitrile prepared above (61.6 g) in ethanol (170 ml) is mixed with a solution of potassium hydroxide (47 g) and water (100 ml) and refluxed for 3.5 hours. The ethanol is evaporated under diminished pressure and the residue dissolved in water (700 ml). The resulting liquid is washed with ether, filtered with charcoal and the filtrate acidified with an excess of hydrochloric acid. After standing overnight, the separated crude 2-(3-trifluoromethyl-4-chlorophenylthio)-phenylacetic acid is filtered, air-dried, and crystallized from a mixture of benzene and light petroleum; m.p. 128°–130° C., yield 58.1 g (89%).

The acid from the preceding experiment (13.0 g) and o-dichlorobenzene (200 ml) are added to polyphosphoric acid, prepared from 85% phosphoric acid (45 ml) and phosphorus pentoxide (90 g), and the vigorously stirred mixture is heated for 16 hours at bath temperature 200° C. After cooling, the mixture is decomposed with water (2.5 l) and extracted with chloroform. The extract is washed with 5% sodium hydroxide solution, dried over sodium sulfate and evaporated. The higher-boiling material, i.e., o-dichlorobenzene, is removed by distillation in vacuo. The residue is dissolved in cyclohexane (70 ml), the insoluble portion filtered off, the filtrate concentrated and allowed to stand in a refrigerator, yielding 5.17 g (42%) of the desired 7-trifluoromethyl-8-chlorodibenzo(b,f)thiepine-10(11H)-one, m.p. 137°–139° C. (cyclohexane-light petroleum). The yield is increased to 50% by working up with mother liquors.

A solution of sodium borohydride (0.24 g) in water (2.5 ml), containing a drop of 20% sodium hydroxide solution, is added to a solution of the above ketone (5.06 g) in a mixture of ethanol (120 ml) and dioxane (25 ml). The stirred mixture is refluxed for 3.5 hours, the solvents evaporated under diminished pressure and the residue shaken between benzene (120 ml) and water (60 ml). The benzene layer is washed with 4% sodium hydroxide solution and water, dried over sodium sulfate and taken down. The crystalline residue (4.92 g; 97%) represents the crude 7-trifluoromethyl-8-chloro-10-hydroxy-10,11-dihydrodibenzo(b,f)thiepine which is purified by crystallization from hexane; m.p. 123°–124° C., yield 4.46 g (88%).

A mixture of the alcohol from the preceding experiment (3.3 g) and thionyl chloride (1.2 ml) is allowed to stand at room temperature for 12 hours and then heated under a reflux condenser in a steam-bath for 1 hour. The reaction mixture is cooled, dissolved in chloroform and the solution washed with water and dried over calcium chloride. Evaporation of the solvent affords crystalline 7-trifluoromethyl-8,10-dichloro-10,11-dihydrodibenzo(b,f)thiepine, melting at 100°–102° C. after crystallization from acetone.

EXAMPLE 29

7-Trifluoromethyl-8-chloro-10-(4-methylpiperazino)-dibenzo(b,f)thiepine

1-Methylpiperazine (8.0 g) was added to a solution of 7-trifluoromethyl-8-chlorodibenzo(b,f)thiepine-10(11H)-one (the preparation of which is described in the preceding Example) (5.17 g) in benzene (40 ml). Then, titanium tetrachloride (1.63 g) in benzene (10 ml) was added dropwise, the mixture refluxed for 24 hours while stirring, cooled and decomposed with water (60 ml). The separated solid was filtered and washed with benzene and water. The benzene layer of the filtrate was separated, washed with water, filtered with charcoal and dried over magnesium sulfate. Evaporation of the benzene yielded 5.68 g (88%) of the crude enamine base, named in the heading of this Example. Neutralization of this base with methanesulfonic acid in ethanol, followed by addition of ether, yielded the crystalline methanesulfonate which crystallized from acetone as a monohydrate; m.p. 267°–270° C.

EXAMPLE 30

8-Chloro-7-methoxy-10-(4-methylpiperazino)-10,11-dihydrodibenzo(b,f)thiepine A mixture of 8,10-dichloro-7-methoxy-10,11-dihydrodibenzo(b,f)thiepine (18.6 g), chloroform (50 ml) and 1-methylpiperazine (24 ml) was gently warmed to form a clear solution. After standing at room temperature for 75 hours, the solution was refluxed for 8 hours. The chloroform was evaporated under diminished pressure, the residue treated with water (100 ml) and extracted with benzene. The extract was washed thoroughly with water and shaken with an excess of 3 N-HCl. The separated hydrochloride of the product was filtered, washed with benzene and added to the acid aqueous layer of the filtrate. This suspension was made alkaline with ammonium hydroxide and the liberated base extracted with benzene. The extract was dried over potassium carbonate and the solvent evaporated under diminished pressure, yielding 19.1 g (85%) of the crude oily product (base) which crystallizes after being dissolved in a small volume of ethanol. Crystallization from acetone yields the pure product, m.p. 121°–124° C. Neutralization with maleic acid in ethanol yields the crystalline maleate which is purified by crystallization from methanol; m.p. 169°–172° C.

The required starting 8,10-dichloro-7-methoxy-10,11-dihydrodibenzo(b,f)thiepine was not described heretofore in the literature. It can be prepared, e.g., starting from the known 5-bromo-2-chloroanisole (W. S. Saari et al: J. Med. Chem. 10, 1008, 1967) by the following sequence of reactions:

A solution of 5-bromo-2-chloroanisole (88.6 g) in tetrahydrofuran (160 ml) is added dropwise during 1.5 hours to magnesium (10.7 g) in tetrahydrofuran (80 ml). The mixture is refluxed for 1.5 hours to complete the formation of the Grignard reagent. Flowers of sulfur (10.5 g) are added in small portions at 22°–25° C. during 1 hour under stirring and the mixture is stirred at room temperature for an additional 30 minutes. After standing overnight, the mixture is refluxed for one hour, cooled and decomposed by pouring on a mixture of ice (600 g) and concentrated hydrochloric acid (120 ml). The product is extracted with benzene and taken from this solvent into aqueous phase by extraction with an excess of 10% sodium hydroxide solution. The alkaline aqueous solution is separated, the product liberated by acidification with hydrochloric acid, again extracted with benzene and the extract dried over sodium sulfate. Distillation yields 40.5 g (58%) of 4-chloro-3-methoxythiophenol, b.p. 149°–153° C./27 Torr.

The thiol from the preceding preparation (19.3 g) is dissolved at 50° C. in a solution of potassium hydroxide (18.8 g) in water (200 ml). 2-Iodobenzoic acid (26.5 g) (W. Wachter, Ber. 26, 1744, 1893), followed by copper powder (freshly reduced) (1 g), is added, the mixture refluxed for 8.5 hours while stirring and filtered while hot. The compound on the filter is washed with hot water and the filtrate acidified with hydrochloric acid. After complete cooling, the separated crude 2-(4-chloro-3-methoxyphenylthio)benzoic acid is filtered, washed with water and crystallized from boiling ethanol (1500 ml). Filtration and work-up of the mother liquors yield 24.2 g (75%) of practically pure compound, m.p. 240°–242° C. The analytically pure product melts at 245°–247° C.

A 50% solution (benzene) of sodium bis(2-methoxyethoxy)aluminum hydride (48 ml) is added dropwise during 30 minutes to a stirred suspension of the above-prepared acid (16.6 g) in benzene (120 ml). The mixture is stirred for 3 hours at room temperature and decomposed by dropwise addition of 10% sodium hydroxide solution (80 ml) under external cooling with ice and water. The product is extracted with benzene, the extract worked up and the crude evaporation residue crystallized from a mixture of benzene and light petroleum, affording 12.5 g (78%) of 2-(4-chloro-3-methoxyphenylthio)benzyl alcohol which in the pure state melts at 78°–80° C.

Thionyl chloride (6.5 g) is added dropwise to a stirred mixture of the alcohol from the preceding preparation (11.2 g) and pyridine (4.0 g) at 10°–20° C. The mixture is stirred at room temperature for 3 hours and, after standing overnight, for one additional hour at 30°–40° C. The cooled mixture is decomposed by dropwise addition of water (20 ml) and the product extracted with benzene. The work-up of the extract, followed by crystallization of the crude residue from a small volume of hexane, yields 10.2 g (85%) of 2-(4-chloro-3-methoxyphenylthio)benzyl chloride which in the pure state melts at 57°–59° C.

A solution of sodium cyanide (2.5 g) in water (5 ml) is added to a solution of the chloride, prepared in the preceding preparation (10.2 g) in ethanol (12 ml), and the mixture refluxed for 8 hours. The ethanol is evaporated under diminished pressure, the residue diluted with water and extracted with benzene. The work-up of the extract and crystallization of the crude residue from ethanol (15 ml) affords 8.83 g (90%) of 2-(4-chloro-3-methoxyphenylthio)phenylacetonitrile. The pure compound melts at 78°–80° C.

A solution of potassium hydroxide (8.25 g) in water (20 ml) is added to a solution of the above-prepared nitrile (8.8 g) in ethanol (30 ml) and the mixture refluxed for 4 hours. The ethanol is evaporated under diminished pressure and the residue diluted with water. The solution is washed with ether, cooled and acidified with hydrochloric acid. The crude product is filtered and crystallized from a mixture of benzene (10 ml) and light petroleum (25 ml), yielding 8.5 g (90%) of 2-(4-chloro-3-methoxyphenylthio)phenylacetic acid. The pure product melts at 103°–105° C.

A solution of the acid from the preceding experiment (6.5 g) in toluene (25 ml) was added to polyphosphoric acid (55 g) and the solution refluxed (bath temperature 150° C.) for 3 hours under stirring. The cooled reaction mixture was decomposed with an ice-water mixture (250 g) and the product extracted with benzene. The benzene solution was washed with 5% sodium hydroxide solution, dried and taken down. Crystallization of the residue from benzene (30 ml) yielded 5.1 g (83%) of the pure 8-chloro-7-methoxydibenzo(b,f)thiepine-10(11H)-one, m.p. 171°–173° C.

A solution of sodium borohydride (0.5 g) in water (3.5 ml), containing 0.1 ml of 15% sodium hydroxide solution was slowly added dropwise to a solution of the ketone from the preceding preparation (6.2 g) in a mixture of benzene (40 ml) and ethanol (100 ml). The stirred mixture was refluxed for 3 hours, the volatile components evaporated under diminished pressure, the residue diluted with water and extracted with benzene. A conventional isolation procedure, followed by crystallization of the crude product from ethanol (25 ml), yielding 5.2 g (83%) of 8-chloro-10-hydroxy-7-methoxy-10,11-dihydrodibenzo(b,f)thiepine, m.p. 130°–132° C.

Powdered anhydrous calcium chloride (3.0 g) was added to a solution of the above-prepared alcohol (3.0 g) in benzene (50 ml) and anhydrous hydrogen chloride introduced into this suspension for 1.5 hour. After standing overnight, the mixture was filtered and the filtrate taken down in vacuo. The residue was crystallized from cyclohexane (35 ml), so yielding 2.25 g (72%) of the desired 8,10-dichloro-7-methoxy-10,11-dihydrodibenzo(b,f)thiepine, m.p. 130°–132° C. The product evidenced a depression in melting point when mixed with the starting compound. The identity of the product was proved by its analysis and NMR spectrum.

EXAMPLE 31

8-Chloro-7-methoxy-10-(4-methylpiperazino)dibenzo(b,f)-thiepine

1-Methylpiperazine (8.2 g) was added to a solution of 8-chloro-7-methoxydibenzo(b,f)thiepine-10(11H)-one (see the preceding Example) (5.1 g) in benzene (50 ml). Then, a solution of titanium tetrachloride (1.8 g) in benzene (15 ml) was added dropwise during 5 minutes while stirring. The stirred mixture was refluxed for 25 hours, cooled and decomposed by dropwise addition of water (70 ml). The separated precipitate was filtered and washed with benzene, the benzene solutions combined, washed with water, filtered with charcoal, dried and taken down. Crystallization of the residue from ethanol (25 ml) yielded 4.92 g (75%) of the desired base which, in the pure state, melts at 144°–146° C. Neutralization with maleic acid in ethanol yielded the crystalline maleate, m.p. 214°–216° C. (ethanol).

EXAMPLE 32

8-Chloro-3,7-difluoro-10-(4-methylpiperazino)-10,11-dihydrodibenzo(b,f)thiepine

A mixture of 8,10-dichloro-3,7-difluoro-10,11-dihydrodibenzo(b,f)thiepine (7.5 g), 1-methylpiperazine (15 ml) and chloroform (15 ml) was warmed until formation of a homogeneous solution, the mixture allowed to stand overnight at room temperature and then refluxed for 8 hours. After cooling, the chloroform was evaporated in vacuo, the residue diluted with benzene (200 ml), the solution thoroughly washed with water and shaken with an excess of 10% hydrochloric acid. The separated hydrochloride was filtered, added to the aqueous layer of the filtrate, and ammonium hydroxide added. The liberated base was extracted with benzene and the usual work-up procedure yielded 7.6 g of the desired oily base which was crystallized from aqueous ethanol and in the pure state melts at 82°–84° C. Neutralization with methanesulfonic acid in a mixture of ethanol and ether gives the crystalline dimethanesulfonate which crystallized from a mixture of 95% ethanol and ether in the form of monohydrate, which melts in the pure state at 150°–152° C. The anhydrous dimethanesulfonate melts at 238°–240° C. with decomposition.

The required starting 8,10-dichloro-3,7-difluoro-10,11-dihydrodibenzo(b,f)thiepine was not previously described in the literature. It can be prepared starting from the known 2-bromo-4-fluorotoluene (M. J. S. Dewar and P. J. Grisdale, J. Org. Chem. 28, 1759, 1963) by the following series of reactions:

A mixture of 2-bromo-4-fluorotoluene (37.4 g), N-bromosuccinimide (39 g), tetrachloromethane (120 ml) and benzoyl peroxide (0.25 g) is refluxed for 5 hours. After standing overnight, the separated succinimide is filtered off and the filtrate is taken down under diminished pressure, yielding 52 g (100%) of crude 2-bromo-4-fluorobenzyl bromide which can be used in the next step without purification. In order to characterize the pure compound, a sample can be distilled; b.p. 127° C./20 Torr.

Sodium cyanide (7.5 g) is added to a solution of the bromide from the preceding preparation (27.4 g) in dimethylformamide (40 ml) under external cooling with cold water and the mixture is stirred at room temperature for 3 hours. After standing overnight, the mixture is diluted with large volumes of water and set aside for several hours. The separated product is filtered, washed with water and dried, yielding 21 g (96%) of crude 2-bromo-4-fluorophenylacetonitrile which is crystallized from cyclohexane. The pure compound melts at 71°–73° C.

A solution of potassium hydroxide (94.6 g) in water (200 ml) is added to a solution of the nitrile from the preceding preparation (71 g) in ethanol (400 ml) and the mixture refluxed for 8 hours. The ethanol is evaporated under diminished pressure and the residue diluted with large volumes of water. A small amount of separated solid is removed by filtration and the filtrate acidified. After standing overnight, the separated 2-bromo-4-fluorophenylacetic acid is filtered, washed with water and dried; m.p. 113°–116° C.; yield 74.2 g (94%). After crystallization from a mixture of benzene and light petroleum, the pure compound melts at 116°–118° C.

4-Chloro-3-fluorothiophenol (see Example 19) (32.6 g) and the acid from the preceding experiment (40 g) are successively added to a solution of sodium ethoxide, prepared from sodium (8.6 g) in ethanol (180 ml). This solution of sodium salts of both the starting compounds is evaporated under diminished pressure and traces of ethanol are removed by heating to 150° C. in a bath. Dimethylformamide (240 ml), copper (6 g) and anhydrous potassium carbonate (10 g) are added to the residue and the stirred mixture heated to 150° C. for 11 hours and then filtered. The filtrate is evaporated in vacuo, the residue diluted with water and the turbid solution washed with benzene to remove hydrophobic material. Acidification of the alkaline solution with hydrochloric acid liberates the oily acid which is extracted with benzene. The conventional work-up of the extract yields 33.0 g of the oily 2-(4-chloro-3-fluorophenylthio)-4-fluorophenylacetic acid, sufficiently pure for further work.

Polyphosphoric acid, prepared from phosphorus pentoxide (90 g) and 85% phosphoric acid (45 ml), was added to a solution of the acid from the preceding preparation (33 g) in toluene (300 ml) and the mixture refluxed for 16 hours under stirring. After cooling, the mixture was decomposed with ice and water, the toluene layer separated, washed with 5% sodium hydroxide solution, dried over magnesium sulfate and evaporated, yielding 34 g of the crude, semi-crystalline 8-chloro-3,7-difluorodibenzo(b,f)thiepine-10(11H)-one which was crystallized from ethanol-benzene and melts at 131°–133° C. when pure.

A solution of sodium borohydride (1.0 g) in water (3 ml) containing 2 drops of 20% sodium hydroxide solution was added dropwise to a stirred solution of the ketone from the preceding experiment (7.9 g) in dioxane (100 ml). The mixture was refluxed for 6 hours, the dioxane evaporated in vacuo and the residue mixed with water and extracted with benzene. Evaporation of the extract and crystallization of the residue from an ether-cyclohexane mixture yielded 6.0 g of the pure 8-chloro-3,7-difluoro-10-hydroxy-10,11-dihydrodibenzo(b,f)thiepine, m.p. 84°–86° C.

Powdered anhydrous calcium chloride (5 g) was added to a solution of the alcohol from the preceding preparation (7.6 g) in methylene chloride (100 ml) and anhydrous hydrogen chloride introduced into the suspension for 2 hours. The mixture was then allowed to stand overnight and filtered. The filtrate was evaporated, yielding 7.5 g of the desired 8,10-dichloro-3,7-difluoro-10,11-dihydrodibenzo(b,f)thiepine which is crystallized from cyclohexane. The pure compound melts at 118.5°–119.5° C.

EXAMPLE 33

8-Chloro-3-fluoro-7-methoxy-10-(4-methylpiperazino)-dibenzo(b,f)thiepine

1-Methylpiperazine (40 ml) was added to a solution of 8-chloro-3-fluoro-7-methoxydibenzo(b,f)thiepine-10(11H)-one (20.3 g) in benzene (160 ml). Titanium tetrachloride (8.0 g) in benzene (20 ml) was added dropwise in the course of 10 minutes, the mixture refluxed for 25 hours under stirring, cooled and decomposed with water. The separated solid was filtered, washed with benzene, the combined benzene solutions being washed with water, dried and evaporated. The oily residue was crystallized from ethanol, yielding 19.3 g of the crude base. After crystallization from ethanol, the pure product melts at 167°–168° C. Neutralization with maleic acid in an ethanol-ether mixture gives the crystalline dimaleate which is crystallized from ethanol; m.p. 204°–205.5° C. (decomposition).

The required starting 8-chloro-3-fluoro-7-methoxydibenzo(b,f)thiepine-10(11H)-one was not previously described in the literature. It can be prepared e.g, by the following procedure:

A mixture of 4-chloro-3-methoxythiophenol (see Example 30) (36.2 g), 2-bromo-4-fluorophenylacetic acid (see the preceding Example) (39.6 g), potassium hydroxide (20 g) and dimethylformamide (250 ml) is heated to 100° C. while stirring until formation of a homogeneous solution. The greatest part of the dimethylformamide is distilled off under normal pressure, removing also the water arising by neutralization. Dimethylformamide (250 ml), anhydrous potassium carbonate (10 g) and copper (6 g) are added to the residue and the mixture is stirred for 14 hours in a bath heated to 170° C. The solvent is evaporated in vacuo, the residue dissolved in water, filtered and the filtrate made acidic by addition of hydrochloric acid. The separated oily acid is extracted with a large volume of warm benzene. The extract is then worked up, yielding 40 g of the crude 2-(4-chloro-3-methoxyphenylthio)-4-fluorophenylacetic acid which is crystallized from aqueous ethanol or cyclohexane. The pure compound melts at 118°–119° C.

A solution of the acid from the preceding preparation (13.8 g) in toluene (200 ml) was added to polyphosphoric acid, prepared from 85% phosphoric acid (25 ml) and phosphorus pentoxide (50 g) and the mixture refluxed for 14 hours under stirring. After cooling, the mixture was decomposed with ice and water and warm toluene (200 ml) added to dissolve the partly separated product. The toluene layer was separated, washed with 5% sodium hydroxide solution and water, dried and evaporated, yielding 11.4 g (88%) of the desired 8-chloro-3-fluoro-7-methoxydibenzo(b,f)thiepine-10(11H)-one. This is crystallized from benzene-ethanol; m.p. 195°–197° C.

EXAMPLE 34

8-Chloro-3-fluoro-7-methoxy-10-(4-methylpiperazino)-10,11-dihydrodibenzo(b,f)thiepine A mixture of 8,10-dichloro-3-fluoro-7-methoxy-10,11-dihydrodibenzo(b,f)thiepine (5.7 g), chloroform (15 ml) and 1-methylpiperazine (15 ml) was warmed until dissolution, set aside for 48 hours at room temperature and then refluxed for 6 hours. After cooling, the chloroform was evaporated in vacuo, the residue being mixed with water and extracted with benzene. The extract was thoroughly washed with water and then shaken with an excess of 10% hydrochloric acid. The separated hydrochloride was filtered, added to the aqueous layer of the filtrate, the suspension made alkaline with ammonium hydroxide and the base extracted with benzene. The work-up of the extract affords 6.5 g of the crude oily base which crystallized from a mixture of cyclohexane and light petroleum as a solvate with ½ cyclohexane molecule, m.p. 135°–136° C. Neutralization of the base with maleic acid in an ethanol-ether mixture gives the crystalline dimaleate which is crystallized from the same mixture of solvents and in the pure state melts at 167°–169° C.

The required starting 8,10-dichloro-3-fluoro-7-methoxy-10,11-dihydrodibenzo(b,f)thiepine is a new compound which can be prepared, e.g., from 8-chloro-3-fluoro-7-methoxydibenzo(b,f)thiepine-10(11H)-one (see the preceding Example) by the following procedure:

A solution of sodium borohydride (0.70 g) in water (2 ml), containing one drop of 20% sodium hydroxide solution was added to a solution of the said ketone (5.6 g) in dioxane (60 ml) and the mixture is stirred at room temperature for 6 hours. After standing overnight, the dioxane was evaporated, the residue diluted with water and extracted with benzene. The extract was worked-up in a conventional manner, yielding 5.45 g of 8-chloro-3-fluoro-10-hydroxy-7-methoxy-10,11-dihydrodibenzo(b,f)thiepine, m.p. 143°–145° C. (benzene).

Anhydrous hydrogen chloride was introduced at 0° C. for 1 hour into a stirred solution of the alcohol from the preceding preparation (5.6 g) in methylene chloride (130 ml). The mixture was stirred for 6 hours at 0° C.

and the separated crystalline product filtered. Further amounts of the product are obtained by concentration of the mother liquor, the total yield of the desired 8,10-dichloro-3-fluoro-7-methoxy-10,11-dihydrodibenzo(b,f)thiepine, m.p. 162°–163° C., being 5.45 g.

EXAMPLE 35

8-Chloro-3-fluoro-7-methoxy-10-(4-methylpiperazino)-10,11-dihydrodibenzo(b,f)thiepine Sodium borohydride (3.2 g) was added to a solution of 8-chloro-3-fluoro-7-methoxy-10-(4-methylpiperazino)dibenzo(b,f)thiepine (see Example 33) (10.7 g) in tetrahydrofuran (50 ml). Acetic acid (18 ml) containing 3% of acetic anhydride, was added dropwise while stirring without cooling in the course of 90 minutes under nitrogen, the temperature of the mixture being 25°–40° C. The mixture was stirred for 30 minutes, then refluxed for 5 hours and allowed to stand overnight. After addition of ether, the mixture was decomposed with 10% sodium hydroxide solution (50 ml), the organic layer being washed with water and shaken with an excess of 10% hydrochloric acid. The separated mixture of the corresponding ketone and the hydrochloride of the product was filtered, added to the aqueous layer of the filtrate and made alkaline with ammonium hydroxide. Extraction with benzene afforded a mixture of the desired base and the corresponding ketone. The latter was removed by crystallization of the mixture from ethanol-benzene. The separated product was the ketone, i.e., 8-chloro-3-fluoro-7-methoxydibenzo(b,f)thiepine-10(11H)-one. The base which is present in the mother liquor, was neutralized with maleic acid, yielding 4.2 g of the dimaleate, m.p. 167°–169° C. The base, liberated from the crystalline dimaleate with ammonium hydroxide and isolated by extraction with benzene, was crystallized from cyclohexane. It formed a solvate with ½ cyclohexane molecule, melting at 135°–136° C. Both the base and the dimaleate were identical with the products prepared in Example 34.

EXAMPLE 36

8-Chloro-3,7-dimethoxy-10-(4-methylpiperazino)dibenzo(b,f)thiepine

1,Methylpiperazine (20 ml) was added to a solution of 8-chloro-3,7-dimethoxydibenzo(b,f)thiepine-10(11H)-one (9.63 g) in benzene (80 ml). A solution of titanium tetrachloride (3.2 g) in benzene (10 ml) was added dropwise and the mixture refluxed for 25 hours and then decomposed with water. The separated compound was filtered and washed with benzene. The combined benzene solutions were dried over potassium carbonate and taken down. The residue represents a mixture of the desired base and the starting ketone. These compounds were separated by the following procedure: The residue was dissolved in a sufficient amount of benzene and the solution shaken with a solution of maleic acid (10 g) in water (200 ml). Whereas the ketone remains dissolved in the benzene layer, the desired base was separated as the solid maleate. This was filtered, suspended in water and the base again liberated by addition of ammonium hydroxide and extracted with benzene. This procedure affords 6.5 g of the crystalline base which was crystallized from a mixture of ethanol and benzene. The pure product melted at 188°–190° C. The maleate was purified by crystallization of the crude salt from ethanol; m.p. 220°–221° C.

The required starting 8-chloro-3,7-dimethoxydibenzo(b,f)thiepine-10(11H)-one is a new compound. It can be prepared, e.g., from 4-chloro-3-methoxythiophenol (see Example 30) and 2-iodo-4-methoxybenzoic acid (see K. Sindelar et al, Collection Czech. Chem. Commun. 39, 3548, 1974) by the following reaction sequence:

4-Chloro-3-methoxythiophenol (65.5 g), followed by 2-iodo-4-methoxybenzoic acid (96.4 g) and copper (5.0 g), is added to a stirred solution of potassium hydroxide (56 g) in water (500 ml). The mixture is refluxed for 6 hours while stirring, filtered while hot and the filtrate acidified with hydrochloric acid. After standing overnight, the separated crude 2-(4-chloro-3-methoxyphenylthio)-4-methoxybenzoic acid is filtered and crystallized from an ethanol-benzene mixture, yielding 94.2 g of the pure compound, m.p. 215°–216° C.

To a stirred suspension of the acid from the preceding preparation (94.2 g) in benzene (600 ml), 55% benzene solution (213 ml) of sodium bis(2-methoxyethoxy)aluminum hydride is added dropwise at 30°–40° C. (under slight cooling) during 1 hour. The mixture is stirred at room temperature for 6 hours, left overnight and decomposed by dropwise addition of 10% sodium hydroxide solution (400 ml). The benzene layer is separated, dried over sodium sulfate and evaporated, yielding crude 2-(4-chloro-3-methoxyphenylthio)-4-methoxybenzyl alcohol in nearly theoretical yield (about 90 g). A sample of this product boils at 215° C./1.5 Torr.

Thionyl chloride (40.5 g) is added dropwise at 10°–20° C. to a stirred solution of the alcohol from the preceding experiment (91 g) in pyridine (30 ml) and chloroform (30 ml) in the course of 1 hour. The mixture is stirred at room temperature for an additional hour, set aside for 48 hours, heated to 40° C. for 2 hours and decomposed with water. The product is isolated by extraction with benzene. The extract affords 86 g of crude oily 2-(4-chloro-3-methoxyphenylthio)-4-methoxybenzyl chloride which is used without purification in the next step.

A solution of sodium cyanide (25 g) in dimethylformamide (200 ml) is added to a solution of the crude chloride from the above experiment (86 g) in dimethylformamide (200 ml) and the mixture is heated to 90° C. and stirred at this temperature for 4 hours. After standing overnight, the separated sodium chloride is filtered off, the filtrate evaporated in vacuo, the residue diluted with water and extracted with benzene. The extract is worked up and the product distilled, yielding 58.5 g of 2-(4-chloro-3-methoxyphenylthio)-4-methoxyphenylacetonitrile, b.p. 230° C./0.8 Torr.

A solution of potassium hydroxide (50 g) in water (60 ml) is added to a solution of the above-prepared nitrile (58.5 g) in ethanol (200 ml) and the mixture refluxed for 5 hours under stirring. The ethanol is evaporated, the residue diluted with water, the solution washed with benzene and the aqueous layer acidified with hydrochloric acid. After standing overnight, the separated crude 2-(4-chloro-3-methoxyphenylthio)-4-methoxyphenylacetic acid is fitered, washed with water and dried. Crystallization from a mixture of benzene and light petroleum yields 62 g of a product with a diffuse melting point, 52°–65° C. Further crystallization from benzene-cyclohexane yields the crystalline solvate with a half cyclohexane molecule which melts first at 50°–65° C. at which temperature it apparently loses the crystal solvent, and then again at 114°–116° C.

A solution of the acid from the preceding experiment (60.8 g) in toluene (600 ml) was added to polyphosphoric acid, prepared from 85% phosphoric acid (90 ml) and phosphorus pentoxide (180 g), and the mixture is refluxed for 8 hours while stirring. After cooling, the toluene layer was decanted and the residue extracted for 5 hours with boiling toluene (400 ml). The toluene solutions are combined, washed rapidly with warm 10% sodium hydroxide solution and warm water, dried briefly over magnesium sulfate and evaporated. The crystalline residue (46.5 g) was crystallized from benzene-ethanol, yielding 40.8 g of the desired 8-chloro-3,7-dimethoxydibenzo(b,f)thiepine-10(11H)-one. The product changed the crystal modification at 177°–178° C. and melted at 186.5°–187.5° C.

EXAMPLE 37

8-Chloro-3,7-dimethoxy-10-(4-methylpiperazino)-10,11-dihydrodibenzo(b,f)thiepine A mixture of 8,10-dichloro-3,7-dimethoxy-10,11-dihydrodibenzo(b,f)thiepine (23 g), chloroform (50 ml) and 1-methylpiperazine (50 ml) was heated until it became homogeneous, set aside for 48 hours, refluxed for 16 hours, cooled, diluted with benzene (300 ml) and washed thoroughly with water. The benzene layer was shaken with an excess of 10% hydrochloric acid and the separated hydrochloride filtered and combined with the acid aqueous layer of the filtrate. This suspension was made alkaline with ammonium hydroxide and the product taken up in benzene. The benzene extract yielded 21.8 g of the crude base which crystallized from ethanol and in the pure state melted at 149°–150° C. Neutralization of this base with maleic acid in a mixture of ethanol and ether yielded the crystalline dimaleate, which melts at 95°–100° C., then solidifies and re-melts at 120°–122° C. (ethanol-ether).

The required starting 8,10-dichloro-3,7-dimethoxy-10,11-dihydrodibenzo(b,f)thiepine was not previously described in the literature. It can be prepared, e.g., from 8-chloro-3,7-dimethoxydibenze(b,f)thiepine-10(11H)-one (see the preceding Example) by the following procedure:

A solution of sodium borohydride (3.5 g) in water (10 ml), containing 2 drops of 20% sodium hydroxide solution was added while stirring to a warm solution of the ketone (22.5 g) in dioxane (200 ml). The mixture was stirred at room temperature for 2 hours and allowed to stand overnight. The dioxane was evaporated in vacuo, the residue mixed with water and the product extracted with benzene. The extract yielded a nearly theoretical amount (22.3 g) of crude 8-chloro-10-hydroxy-3,7-dimethoxy-10,11-dihydrodibenzo(b,f)-thiepine which was crystallized from a mixture of benzene and light petroleum and melts at 105°–106° C. in the pure state.

Anhydrous hydrogen chloride was passed at 0° C. into a stirred solution of the alcohol from the above experiment (22.5 g) in methylene chloride (500 ml) for 3 hours. Anhydrous calcium chloride (5 g) was added, the mixture stirred at room temperature for 3 hours and filtered. The filtrate was evaporated under diminished pressure, yielding 23.4 g of crude 8,10-dichloro-3,7-dimethoxy-10,11-dihydrodibenzo(b,f)-thiepine. The compound was crystallized from methylene chloride and melted in the pure state at 151°–153° C.

What is claimed is:

1. A compound of the formula

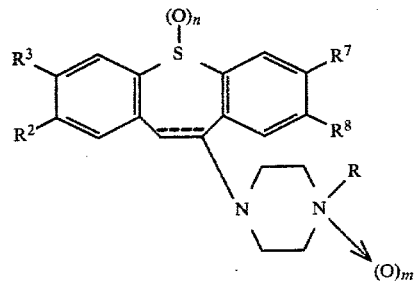

wherein $R^2$, $R^3$, $R^7$ and $R^8$ are selected from the group consisting of hydrogen, fluorine and chlorine atoms, a trifluoromethyl group, a methoxy group and a hydroxyl group, the relationship between $R^2$, $R^3$, $R^7$ and $R^8$ being such that (a) $R^2$ and $R^3$ are other than hydrogen, (b) $R^7$ and $R^8$ are other than hydrogen, or (c) at least three of the substituents $R^2$, $R^3$, $R^7$ and $R^8$ are other than hydrogen, R being selected from the group consisting of hydrogen, an alkyl group having from 1-3 carbon atoms, a hydroxyalkyl, a hydroxyalkyl group having from 1-3 carbon atoms, an acyloxyalkyl group having from 8-10 carbon atoms in the acyl moiety and from 2-3 carbon atoms in the alkyl moiety and an ethoxycarbonyl group, m and n being selected from the group consisting of 0 and 1, and the bond between carbon atoms 10 and 11 being selected from the group consisting of single bonds and double bonds, and salts thereof determined by neutralization with an acid selected from the group consisting of maleic acid and methanesulfonic acid.

2. 8-chloro-7-fluoro-10-(4-methylpiperazino)dibenzo(b,f)thiepine.
3. 8-chloro-7-fluoro-10-(4-methylpiperazino)-10,11-dihydrodibenzo(b,f)thiepine.
4. 7,8-difluoro-10-(4-methylpiperazino)dibenzo(b,f)thiepine.
5. 7,8-difluoro-10-(4-methylpiperazino)-10,11-dihydrodibenzo(b,f)thiepine.
6. 7-chloro-8-fluoro-10-(4-methylpiperazino)dibenzo(b,f)thiepine.
7. 7,8-dichloro-10-[4-(3-octanoyloxypropyl)-piperazino]-10,11-dihydrodibenzo(b,f)thiepine.
8. 8-chloro-2,3-dimethoxy-10-(4-methylpiperazino)-10,11-dihydrodibenzo(b,f)thiepine.
9. 8-chloro-2,3-dihydroxy-10-(4-methylpiperazino)-10,11-dihydrodibenzo(b,f)thiepine.
10. 8-chloro-2,3-dimethoxy-10-(4-methylpiperazino)-10,11-dihydrodibenzo(b,f)thiepine-5-oxide.
11. 8-chloro-7-fluoro-10-[4-(2-hydroxyethyl)-piperazino]-10,11-dihydrodibenzo(b,f)thiepine-$N^4$-oxide.
12. 8-chloro-3,7-difluoro-10-(4-methylpiperazino)-10,11-dihydrodibenzo(b,f)thiepine.

* * * * *